United States Patent [19]

Jones et al.

[11] 4,255,405

[45] Mar. 10, 1981

[54] NAPHTHOQUINONE ANTI-PSORIATIC AGENTS

[75] Inventors: Gordon H. Jones, Cupertino; John Young, Redwood City, both of Calif.

[73] Assignee: Syntex (U.S.A.) Inc., Palo Alto, Calif.

[21] Appl. No.: 43,090

[22] Filed: May 29, 1979

Related U.S. Application Data

[63] Continuation-in-part of Ser. No. 912,697, Jun. 5, 1978.

[51] Int. Cl.³ .............................................. A61K 31/22
[52] U.S. Cl. ................................... 424/311; 424/304
[58] Field of Search ...................... 424/311, 304, 331; 260/396 R

[56] References Cited

U.S. PATENT DOCUMENTS 3,914,264  10/1975  Marisco et al. ................. 260/396 R
4,115,584   9/1978  Bellina et al. ...................... 424/301

OTHER PUBLICATIONS

Chemical Abstracts 9th Coll. Formula Index (1972–1976), 6798 F Col. 1 & 80:145864W (1974).
Chemical Abstracts 67:87929q (1967).
Journal of Bidchemistry, vol. 62, No. 2, 1967; pp. 215–222.

*Primary Examiner*—Leonard Schenkman
*Attorney, Agent, or Firm*—Tom M. Moran; Alan M. Krubiner

[57] ABSTRACT

The 2,3-diesters of 6-substituted-2,3-dihydroxy-1,4-naphthoquinones exhibit useful anti-psoriatic activity in mammals.

10 Claims, No Drawings

NAPHTHOQUINONE ANTI-PSORIATIC AGENTS

This application is a continuation-in-part of co-pending U.S. Ser. No. 912,697 filed June 5, 1978.

BACKGROUND OF THE INVENTION

1. Field of the Invention

This invention relates to novel naphthoquinone compositions and the pharmaceutical use of the naphthoquinones in treating psoriasis in a mammal.

2. Prior Art

Psoriasis is a skin disease characterized in part by excessive proliferation of cells of the epidermis which remain strongly adherent and build up into a scaly plaque typical of the disease. Currently available therapies, which are not curative, depend on the control of epidermal cell proliferation through the use of hormonal agents, such as corticosteroids, or through the use of compounds related to cancer chemotherapy such as hydroxyurea, methotrexate, and the nitrogen mustards.

While the above agents are effective to a certain extent, they cause numerous severe undesirable side effects both locally and systemically.

Certain naphthoquinones which are chemically related to the compound of this invention are known. For example, the compound 6-bromo-2,3-dihydroxy-1,4naphthoquinone has been reported by Weygand, German Pat. No. 859,008. While this compound is recognized as a valuable intermediate for the preparation of dyestuffs, no useful biological activity has been ascribed to it. Specifically, any suggestion that this compound might have anti-psoriatic activity has not been advanced.

Related naphthoquinones having antifungal and antibacterial activity can be found in U.S. Pat. No. 3,914,264 and West German Offenlegungschrift Nos. 2,135,712, 2,456,655 and 2,520,739. However, none of these disclosures have recognized the use of these or related naphthoquinone compositions as anti-psoriatic agents.

It is also suggested that certain related compounds have antimalarial activitu, e.g. 6-chloro-2-hydroxy-1,4-naphthoquinone, 7-chloro-2-hydroxy-1,4-naphthoquinone and 6-chloro-1,2,4-triacetoxynaphthoquinone. See L. F. Fieser and R. H. Brown, J. Am. Chem. Soc. 71, 3615–3617 (1949).

It has now been discovered that the 2,3-diesters of 6-substituted-2,3-dihydroxy-1,4-naphthoquinone are effective in preventing epidermal cell proliferation when topically applied to a mammal. More specifically, it is effective as an anti-psoriatic agent in humans.

In its broadest aspect, the present invention is a pharmaceutical composition comprising at least one pharmaceutically acceptable excipient and a 2,3-diester of a 6-substituted-2,3-dihydroxy-1,4-naphthoquinone represented by Formula (I), below,

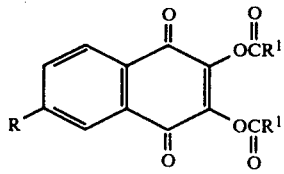
(I)

wherein R is hydrogen, halo, cyano, C1 to C18 linear or branched alkoxy and $R^1$ is an alkyl of 1–5 carbon atoms. Preferably R is halo (particularly chloro) and $R^1$ is alkyl of 1 or 2 carbon atoms.

Another aspect of this invention is a method for preventing epidermal cell proliferation in a mammal which comprises topically administering a composition of the invention to a mammal in need of such treatment.

Formulation and Administration

The compounds useful in the present invention are formulated for administration in any convenient way by analogy with other topical compositions. These compositions may be presented for use in any conventional manner with the aid of any of a wide variety of pharmaceutical excipients.

Generally, the psoriatic manifestation in mammals, particularly humans, is combatted by contacting the afflicted area with a therapeutically effective amount of the naphthoquinone-containing composition of this invention, that is, an amount which reduces the proliferation of epidermal cells (an anti-psoriatic effect). Preferably, the naphthoquinone is first formulated to prepare a suitable pharmaceutical formulation, as discussed hereinafter, which is then placed in contact with an afflicted area. An effective amount of the naphthoquinone will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to effect an anti-psoriatic response, but not enough to adversely effect the recipient, is applied to the afflicted area(s).

The naphthoquinone of this invention may be formulated with suitable pharmaceutical vehicles known in the art to form particularly effective topical compositions. As disclosed above, an effective amount of the naphthoquinone is about 0.001% w to about 10% w of the total formulated composition. The rest of the formulated composition will be about 90% w to about 99.999% w of at least one suitable pharmaceutical excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylene carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthoquinones therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

Water/glycol mixture (15% or more glycol): 50-99 parts by weight
Fatty Alcohol: 1-20
Non-ionic Surfactant: 0-10
Mineral Oil: 0-10
Typical Pharmaceutical Adjuvants: 0-5
Active Ingredients: 0.001-10

The fatty alcohol, non-ionic surfactant, and other adjuvants are discussed in U.S. Pat. No. 3,934,013 to Poulsen which is incorporated herein by reference.

The naphthoquinones of this invention may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

White Petrolatum: 40-94 parts by weight
Mineral Oil: 5-20
Glycol Solvent: 1-15
Surfactant: 0-10
Stabilizer: 0-10
Active Ingredients: 0.001-10.0

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

Active Ingredients: 0.001-10.0 parts by weight
Propylene Carbonate: 1-10
Solvent: 1-10
Surfactant: 0-10
White Petrolatum: 70-97

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

Glycol Solvent: 40-35 parts by weight
Fatty Alcohol: 15-45
Compatible Plasticizer: 0-15
Compatible Coupling Agent: 0-15
Penetrant: 0-20
Active Ingredients: 0.001-10.0

Process For Preparation

The naphthoquinones represented by Formula (I) wherein R is hydrogen, halo, cyano or $C_1$–$C_{18}$ alkoxy are prepared by following, in principle, the process disclosed in the aforesaid Weygand Patentshrift and illustrated by the following Reaction Sequence:

REACTION SEQUENCE 1

Initially, the methyl groups of the 4-substituted ortho-xylene (compounds 1) are directly halogenated. Disubstitution of halo on each of these groups is found to be most facile when bromo is the desired halo substituent. The reaction occurs readily using N-bromosuccinimide as the brominating agent. See for example, Djerassi, Chem. Revs., 43, 271 (1948). Compound 2, the 4-substituted-$\alpha$, $\alpha$, $\beta$, $\beta$-tetrabromo-o-xylene, is next dehalogenated in a manner known for the hydrolysis of gem-dihalides in the presence of a suitable catalyst. The catalysts include, for example, calcium carbonate, sulfuric acid, morpholine and various silver salts. Typically a mixture of acetic acid, compound 2 and silver acetate is heated, resulting in dehalogenating compound 2 to compound 3 which is readily converted to compound 4 typically with base such as sodium bicarbonate. The 4-substituted-1,2-phthalic aldehyde intermediate (4) is next converted to the 6-substituted-2,3-dihydroxy-1,4-naphthoquinone compound 5 by reaction with glyoxal (OHCCHO). This reaction is reported in some detail in the aforesaid Weygand Patenshrift No. 859,008, which is incorporated herein by reference. Generally the reaction is carried out in an aqueous base at a pH of between 8 and 12 and at temperatures of 10° to 80° C. The bases which are employed include alkali metal carbonates, bicarbonates and hydroxides, tertiary amines and the like.

The compounds of Formula (I) wherein $R^1$ alkyl of 1-5 carbon atoms prepared by esterifying the 2,3-dihydroxy compound using methods known in the art. For example, with acyl anhydride or chloride in pyridine solution or in an inert solvent such as tetrahydrofuran containing a tertiary base such as pyridine or triethylamine or with acyl anhydride in the presence of an acid catalyst such as zinc chloride, sulfuric acid or 70% perchloric acid. Suitable acyl anhydrides and acyl chlorides include, for example, acetic anhydride, propionic anhydride, butyl anhydride, valeryl anhydride, caproyl anhydride, acetyl chloride, propionyl chloride, butyryl chloride, valeroyl chloride, caproyl chloride and the like.

The compounds of Formula (I) wherein R is defined as in Reaction Sequence 1 are also prepared by oxidizing 6-substituted-2-hydroxy-1,4-naphthoquinone or 7-substituted-2-hydroxy-1,4-naphthoquinone according to Reaction Sequence 2.

REACTION SEQUENCE 2

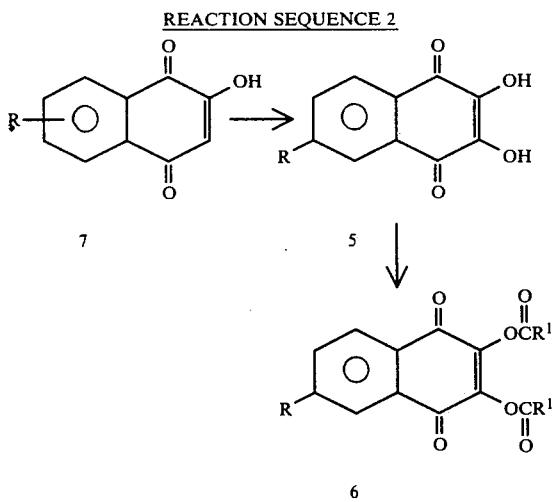

Generally the precursors 7 are known compounds. See, for example, J. Am. Chem. Soc. 71, 3615–17 (1949) and J. Am. Chem. Soc. 75, 2910–15 (1953). The oxidation is suitably carried out by employing methods known in the art such as basic hydrogen peroxide, peracids, e.g., peracetic acid, m-chloroperbenzoic acid, potassium ferricyanide aqueous in alkaline solution, and the like, preferably basic hydrogen peroxide.

In the specification and claims the term "$C_1$ to $C_{18}$ linear or branched alkoxy" is intended to mean alkoxy groups containing 1 to 18 carbon atoms including straight chain groups, branched chain groups and straight or branched chain groups optionally having an optionally substituted phenyl group. Illustrative of such groups are, for example, methoxy, ethoxy, n-propoxy, isopropoxy, n-hexoxy, 2-methylpentoxy, n-octoxy, benzyloxy, 4-methylbenzyloxy, 4-chlorobenzyloxy and the like. The term "halo" refers to the radicals fluoro, chloro, bromo and iodo.

For Preparations 1 and 2 and Examples 1 and 2, reference should be made to the Reaction Sequence 1.

PREPARATION 1

A. 4-Chloro-α,α,β,β-tetrabromo-o-xylene

A mixture of 4-chloro-o-xylene (1: 14.0 g, 0.1 mol) and freshly recrystallized N-bromosuccinimide (80 g, 0.45 mol) in carbon tetrachloride (1 L) is irradiated for 2½ hours (hr) with a 250 watt tungsten infrared lamp positioned so that the solvent refluxed gently. The solid material is then removed by filtration, the filtrate is concentrated in vacuo and the crystalline residue is recrystallized from isopropanol giving 34 g (75%) of 4-chloro-α, α, β, β-tetrabromo-o-xylene (2), melting point (mp) 108°–111° C. [Bull. Soc. Chim., 2966 (1966), mp 114°].

B. In like manner, but substituting
o-xylene
4-bromo-o-xylene
4-fluoro-o-xylene
4-cyano-o-xylene
4-methoxy-o-xylene
4-ethoxy-o-xylene
4-butoxy-o-xylene
4-hexyloxy-o-xylene and
4-undecyloxy-o-xylene for 4-chloro-o-xylene, the following compounds are obtained:
α, α, β, β-tetrabromo-o-xylene,
4-bromo-α, α, β, β-tetrabromo-o-xylene,
4-fluoro-α, α, β, β-tetrabromo-o-xylene,
4-cyano-α, α, β, β-tetrabromo-o-xylene,
4-methoxy-α, α, β, β-tetrabromo-o-xylene,
4-ethoxy-α, α, β, β-tetrabromo-o-xylene,
4-butoxy-α, α, β, β-tetrabromo-o-xylene,
4-hexyloxy-α, α, β, β-tetrabromo-o-xylene, and
4-undecyloxy-α, α, β, β-tetrabromo-o-xylene.

PREPARATION 2

A. 4-Chloro-1,2-phthalic aldehyde

A mixture of 2 (22.8 g, 0.05 mol), silver acetate (36.6 g, 0.22 mol) and glacial acetic acid (500 ml) is heated under reflux for 1½hr. The silver salts are filtered off, washed with chloroform and the combined filtrates concentrated to dryness in vacuo. The last traces of acetic acid are removed from the residue by evaporation with toluene. The resultant semicrystalline material 3 is dissolved in dioxane (500 ml) and a solution of sodium carbonate (53 g) in water (500 ml) is added. This mixture is shaken vigorously at 22° for 20 minutes, saturated with sodium chloride and then extracted with ethyl acetate (2×500 ml). The combined organic extracts are washed with brine (2×400 ml), dried with MgSO$_4$ and concentrated in vacuo giving 6.0 g (72%) of almost pure 4-chloro-1,2-phthalic aldehyde. Sublimation at 75° and 0.05 mm Hg affords 5.4 g of 4, with mp 72°–76°.

B. In like manner, but substituting the compounds prepared in Part B of Example I for 4-chloroα, α, β, β-tetrabromo-o-xylene, the following compounds are prepared:
1,2-phthalic aldehyde,
4-bromo-1,2-phthalic aldehyde,
4-fluoro-1,2-phthalic aldehyde,
4-cyano-1,2-phthalic aldehyde,
4-methoxy-1,2-phthalic aldehyde,
4-ethoxy-1,2-phthalic aldehyde,
4-butoxy-1,2-phathalic aldehyde,
4-hexyloxy-1,2-phthalic aldehyde, and
4-undecyloxy-1,2-phthalic aldehyde.

EXAMPLE 1

A. 6-Chloro-2,3-dihydroxy-1,4-naphthoquinone

A solution of sodium carbonate (12.3 g) in water (290 ml) is added at room temperature to a vigorously stirred solution of 4-chloro-1,2-phthalic aldehyde (4.88 g, 29 mmol) in an oxygen atmosphere followed immediately by the addition, over a five minute period, of a solution of glyoxal bisulfite (16.4 g, 58 mmol) and potassium cyanide (1.88 g, 29 mmol) in water (290 ml). The reaction mixture is stirred in the oxygen atmosphere for a further 5 minutes. It is then treated with 6 N hydrochloric acid (50 ml), cooled in an ice-salt bath and further diluted with water (500 ml). The crystalline product is collected by filtration, washed with water, dried and recrystallized from water:methanol (2:1) giving 3.56 g (55%) of 6-chloro-2,3-dihydroxy-1,4-naphthoquinone, mp 228°–229°.

B. In like manner, by substituting the other 1,2-phthalic aldehydes of Part B, Preparation 2 for 4-chloro-1,2-phthalic aldehyde, the following compounds are obtained:
2,3-dihydroxy-1,4-naphthoquinone,
6-bromo-2,3-dihydroxy-1,4-naphthoquinone,
6-fluoro-2,3-dihydroxy-1,4-naphthoquinone,
6-cyano-2,3-dihydroxy-1,4-naphthoquinone,
6-methoxy-2,3-dihydroxy-1,4-naphthoquinone,
6-ethoxy-2,3dihydroxy-1,4-naphthoquinone,
6-butoxy-2,3-dihydroxy-1,4-naphthoquinone,
6-hexyloxy-2,3-dihydroxy-1,4naphthoquinone, and 6-undecyloxy-2,3-dihydroxy-1,4-naphthoquinone.

EXAMPLE 2

Since known effective anti-psoriasis agents inhibit epidermal cell proliferation, an animal assay using young male rats has been developed wherein the test agent in an appropriate carrier is applied to the skin of one flank of the test animal while the carrier alone is applied to the other flank, i.e., the control. At a suitable time interval after one or more applications of the composition, the skin is removed from the animal and skin plugs taken from both the treated and the control areas are incubated in vitro with tritium labelec thymidine (a precursor of DNA synthesis). A comparative measure of the amount of radio-labeled thymidine incorporated into the DNA of plugs from the treated and control flanks gives a measure of the degree of inhibition of DNA synthesis and hence epidermal cell proliferation which has occurred in response to the treatment.

Compositions illustrative of the compositions of the present invention are tested in the rat in the method disclosed above. The tests are specifically carried out as follows:

Male albino rats, 21–22 days old are shaved on the back and both flanks with electric clippers twenty-four hours prior to testing. A suitable 2,3-diacyloxy-6sub-stituted-11,4,-naphthoquinone is dissolved in a mixture of ethanol (EtOH), acetone, dimethyl sulfoxide (DMSO) or mixture of DMSO and EtOH. Solutions (0.10 ml) containing the test agent, are applied to the right flank of the animals and the carrier alone (0.10 ml) is applied to the left flank. The area covered is approximately 10 sq. cm. Applications are made seven hours apart on days 1, 2 and 3. On day 4 the animals are sacrificed by carbon dioxide asphyxiation, and the full thickness skin from the back and both flanks is removed. Subcutaneous fat and muscle are scraped away and plugs consisting of epidermis and dermis, 6 mm. in diameter are punched out, five from the control flank and five from the treated flank. These are incubated at 37° C. individually floating on 3 ml of Dulbecco's Modified Eagle Medium containing tritiated thymidine (10 microcuries/milliliter). After two hours incubation of plugs are frozen, thawed, blotted dry, rinsed 3 times in 30% aqueous acetic acid and once in absolute ethanol to remove unincorporated tritiated thymidine. The washed plugs are digested in NCS solubilizer for liquid scintillation counting in order to determine the amount of tritiated thymidine incorporated into the DNA. The inhibitory effect of the treatment is determined by comparing the amount of radioactivity incorporated into plugs from the treated side with that incorporated into plugs from the control flank. For each test at least two animals are used. The data are recorded for each animal as the ratio of mean radioactivity is the treated side to the mean radioactivity of the control side (X100).

The amount of tritiated thymidine incorporated is primarily due to epidermal cells, and hence the amount of radioactivity in these tests is directly related to the number of cells (epidermal) engaged in proliferation (DNA synthesis) at the moment of sacrifice. As noted earlier, epidermal cell hyper-proliferation is symptomatic of psoriasis. The compounds useful in the composition of this invention show inhibitory activity against epidermal cell proliferation and as a result are antipsoriatic agents.

EXAMPLE 3

A solution of 1.2 gm 6-chloro-2-hydroxy-1,4-naphthoquinone (or 7-chloro or mixture thereof) and 0.48 g sodium bicarbonate in 58 ml of water is cooled to 5° C. and 2.3 ml of 30% hydrogen peroxide is added in one portion. The mixture is then stirred at 22° C. for 16 hours where the red crystalline product (0.24 g) is removed by filtration and crystallized from water:methanol (2:1) giving the 6-chloro-2,3-dihydroxy-1,4-naphthoquinone, m.p. 228°–229° C.

EXAMPLE 4

A. Concentrated sulfuric acid (0.1 ml) is added to a suspension of 1 g of 6-chloro-2,3-dihydroxy-1,4-naphthoquinone in 5 ml of acetic anhydride and the mixture is gently shaken at 22° C. until a clear, pale yellow solution is obtained (less than 5 minutes). After a further 5 minutes at 22° C. the solution is poured into 250 ml of saturated sodium bicarbonate solution and the yellow crystalline material is collected by filtration, washed well with water and dried in vaccuo giving 1.05 g of a product having a melting point of 109°–110° C. Recrystallization from ethyl acetate/hexane (1:2) gives 2,3-diacetoxy 6chloro-1,4-naphthoquinone, m.p. 110°–111° C.

B. In like manner, but substituting the compounds of Example 1, Part B for 6-chloro-2,3-dihydroxy-1,4-naphthoquinone
2,3-diacetoxy-1,4-naphthoquinone,
2,3-diacetoxy-6bromo-1,4-naphthoquinone,
2,3-diacetoxy-6fluoro-1,4-naphthoquinone,
2,3-diacetoxy-6cyano-1,4-naphthoquinone,
2,3-diacetoxy-6methoxy-1,4-naphthoquinone,
2,3-diacetoxy-6ethoxy-1,4-naphthoquinone,
2,3-diacetoxy-6-butoxy-1,4-naphthoquinone,
2,3-diacetoxy-6hexyloxy-1,4-naphthoquinone, and
2,3-diacetoxy-6undecyloxy-1,4-naphthoquinone.

EXAMPLE 5

Concentrated sulfuric acid (0.1 ml) is added to a suspension of 1 g of 6chloro-2,3-dihydroxy-1,4-naphthoquinone in 5 ml of caproic anhydride and the mixture is gently shaken at 22 C. until a clear, pale yellow solution is obtained (less than 5 minutes). After a further 10 minutes at 22 C. the solution is poured into 250 ml of saturated sodium bicarbonate solution. The organic layer is extracted with ethylacetate which is then evaporated from the solution. The resulting product (2,3-dicaproyloxy-6-chloro-1,4-naphthoquinone) is purified by thin layer chromatography using an elution mixture of 9parts hexane and 1 part ether (volume/volume) which results in an RF value of 0.62.

EXAMPLE 6

By following in principle the appropriate procedures of Example 4, Parts A and B or Example 5, but substituting other acyl anhydrides for acetic anhydride and caproic anhydride, such as propionic anhydride, butyric anhydride or valeric anhydride, the following compounds are obtained:

6-chloro-2,3-dipropionyloxy-1,4-naphthoquinone,
6-chloro-2,3-dibutyroxy-1,4-naphthoquinone,
6-chloro-2,3-divaleryloxy-1,4-naphthoquinone,
6-bromo-2,3-dipropionyloxy-1,4-naphthoquinone,
6-fluoro-2,3-dipropionyloxy-1,4-naphthoquinone,
6-cyano-2,3-dipropionyloxy-1,4-naphthoquinone,
6-methoxy-2,3-dipropionyloxy-1,4-naphthoquinone,
6-hexyloxy-2,3-dipropionyloxy-1,4-naphthoquinone,
and the like.

What is claimed is:

1. A pharmaceutical composition for relieving a condition of psoriasis in a mammal in a form suitable for topical administration to said mammal which comprises at least one pharmaceutically acceptable, non-toxic excipient and a psoriasis-relieving amount of a compound selected from those represented by the formula

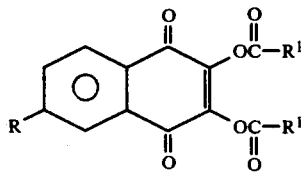

wherein R is hydrogen, halo, cyano or $C_1$ to $C_{18}$alkoxy and $R^1$ is alkyl of one to five carbon atoms.

2. The composition of claim 1 wherein $R^1$ is alkyl of one or two carbon atoms.

3. The composition of claim 1 or 2 wherein R is halo.

4. The composition of claim 1 wherein R is chloro and $R^1$ is alkyl of one or two carbon atoms.

5. The composition of claim 4 wherein $R^1$ is methyl, namely 2,3-diacetoxy-6-chloro-1,4-naphthoquinone.

6. A method for relieving the condition of psoriasis in a mammal which comprises topically administering to said mammal a therapeutically effective amount of a compound selected from those represented by the formula

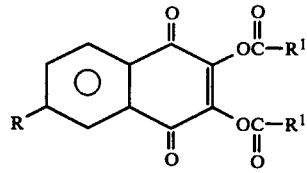

wherein R is hydrogen, halo, cyano or $C_1$ to $C_{18}$alkoxy and $R^1$ is alkyl of one to five carbon atoms.

7. The method of claim 6 wherein $R^1$ is alkyl of one or two carbon atoms.

8. The method of claim 6 wherein R is halo.

9. The method of claim 6 wherein R is chloro and $R^1$ is alkyl of one or two carbon atoms.

10. The method of claim 9 wherein $R^1$ is methyl, namely 2,3-diacetoxy-6-chloro-1,4-naphthoquinone.

* * * * *